US012740872B2

(12) United States Patent
Rivera et al.

(10) Patent No.: US 12,740,872 B2
(45) Date of Patent: Sep. 22, 2026

(54) IMPLANT REMOVAL TOOL

(71) Applicant: TSJ Designs, LLC, Scottsdale, AZ (US)

(72) Inventors: Jose Samuel Rivera, Naples, FL (US); Gerhard Rivera, Orlando, FL (US)

(73) Assignee: TSJ Designs, LLC, Scottsdale, AZ (US)

( * ) Notice: Subject to any disclaimer, the term of this patent is extended or adjusted under 35 U.S.C. 154(b) by 0 days.

(21) Appl. No.: 19/373,902

(22) Filed: Oct. 30, 2025

(65) Prior Publication Data

US 2026/0183124 A1 Jul. 2, 2026

Related U.S. Application Data

(63) Continuation-in-part of application No. 19/002,133, filed on Dec. 26, 2024.

(51) Int. Cl.
*A61F 2/46* (2006.01)
*A61B 17/16* (2006.01)

(52) U.S. Cl.
CPC .... *A61F 2/4609* (2013.01); *A61F 2002/4627* (2013.01)

(58) Field of Classification Search
CPC ............ A61F 2/4609; A61F 2002/4627; A61F 2002/4619; A61B 17/1666
See application file for complete search history.

(56) References Cited

U.S. PATENT DOCUMENTS

| | | | | |
|---|---|---|---|---|
| 3,147,749 A * | 9/1964 | Marsh | A61B 17/32053 | 600/564 |
| 3,628,522 A * | 12/1971 | Kato | A61B 10/0291 | 600/564 |
| 2011/0152868 A1* | 6/2011 | Kourtis | A61B 17/025 | 606/80 |

* cited by examiner

*Primary Examiner* — Tracy L Kamikawa
(74) *Attorney, Agent, or Firm* — Anton J. Hopen; Trenam Law

(57) ABSTRACT

An implant removal tool designed for efficient and precise removal of an acetabular cup or similar implants is disclosed. The tool includes an outer shaft and an internal shaft configured to move relative to the outer shaft. The internal shaft is operably connected to a cutting assembly comprising multiple inwardly curving, wedge-shaped blades. The blades transition from a retracted position to a closed position, forming a semicircular cutting path slightly larger than the outer diameter of the implant. This configuration allows for controlled rotation of the blades around the implant's outer surface, effectively severing surrounding bone while minimizing damage to adjacent bone and soft tissues. The tool may include interchangeable components to accommodate implants of varying sizes, ensuring adaptability across surgical scenarios. Additional features, such as a helical thread mechanism or drill compatibility, enhance usability and precision during revision surgeries.

20 Claims, 17 Drawing Sheets

102
120
115
112
111
110
118
114
116

112
115
110
111
119
118
102
114

IMPLANT REMOVAL TOOL

PRIORITY INFORMATION

This nonprovisional application is a continuation-in-part of and claims priority to non-provisional application Ser. No. 19/002,133, entitled "Implant Removal Tool," filed Dec. 26, 2024, by the same inventor(s).

BACKGROUND OF THE INVENTION

Field of the Invention

This invention relates, generally, to medical devices. More specifically, it relates to implant extraction devices.

Brief Description of the Prior Art

Joint arthroplasty has become increasingly prevalent in the United States and worldwide, particularly for hip, knee, and shoulder replacements. Hip arthroplasty, which involves replacing the acetabulum (hip socket) and femoral head with prosthetic components, is among the most common procedures. During this surgery, an acetabular cup is implanted into the acetabulum to serve as the new socket for the femoral head. The acetabular cup is often coated or textured to promote osseointegration, ensuring it is securely affixed to the bone over time.

Most hip replacements have a lifespan of approximately 25 years. As life expectancy increases, many patients outlive their prosthetic implants, necessitating revision surgeries to repair or replace worn components. Revision surgeries are inherently more complex than the initial arthroplasty due to the presence of bone growth into the implants, making removal challenging. In particular, the removal of the acetabular cup often requires precise surgical techniques to minimize damage to the surrounding bone and soft tissues. Preserving bone structure during revision surgery is critical for ensuring the successful implantation of the replacement prosthetic, reducing recovery time, and lowering the risk of complications.

Various tools and methods have been developed to aid in the removal of prosthetic components during revision surgeries. Despite these advances, existing tools and methods exhibit several limitations. Most rely heavily on the surgeon's technique and do not sufficiently account for the specific geometry of the acetabular cup or the need to minimize bone loss. The device of the present disclosure seeks to address these shortcomings by providing a specialized tool for removing the acetabular cup component with greater precision and efficiency while preserving as much bone as possible. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved implant removal tool and method of use is now met by a new, useful, and nonobvious invention.

The present invention includes an implant removal tool. The tool includes a cutting assembly having a plurality of blades with each blade having an inwardly curving, wedge shape that tapers to a sharp point for cutting bone. In some embodiments, each blade has a curvature that generally matches the curvature of a predetermined implant.

The plurality of blades are moveable between a retracted position and a closed position in which the blades come together to form a closed semicircle that defines a semicircular cutting path. The semicircular cutting path has a diameter that is greater than an outer diameter of an implant with the difference between the semicircular cutting path diameter and the outer diameter of the implant being sufficient to facilitate cutting bone surrounding the implant.

The tool further includes an outer shaft and an internal shaft residing at least partially within the outer shaft and configured to move relative to the outer shaft. The cutting assembly is in operable communication with the internal shaft such that manipulation of the internal shaft causes the plurality of blades to rotate between the retracted position and the closed position.

The tool may further include a handle extending laterally from an outer surface of the outer shaft. The tool may also include a shank extending from a proximal end of the internal shaft beyond the proximal end of the outer shaft, thereby providing a user with a component to manipulate the internal shaft. In some embodiments, the shank is configured to operably engage a drill or hammer drill.

The present invention may further include a helical thread on an internal surface of the outer shaft and a corresponding helical thread on an external surface of the internal shaft. As a result, rotation of the internal shaft relative to the outer shaft causes the internal shaft to move in a longitudinal direction relative to the outer shaft.

In some embodiments, the cutting assembly further includes a translation-support structure in operable engagement with the internal shaft such that translation of the internal shaft causes translation of the translation-support structure. In addition, one or more support arms extends between the translation-support structure and the plurality of blades such that translation of the translation-support structure causes rotation of the plurality of blades. Furthermore, the outermost lateral expanse of the cutting assembly in some embodiments is established by diametrically opposed outer surfaces of a pair of blades from the plurality of blades.

In some aspects, the present disclosure relates to tools and systems for removing implants, and more particularly to implant removal tools having blade geometries configured to self-center about an implant and improve cutting performance. The disclosed tools provide enhanced stability, clearance, and torque efficiency during removal procedures while minimizing the incision size and the likelihood of blade binding against the implant surface.

In some embodiments, an implant removal tool includes at least one shaft in operable communication with a cutting assembly. The cutting assembly includes a plurality of blades, each having an inwardly curving, wedge-shape that tapers to a distal point. At least one of the blades includes a lateral side with a non-linear taper extending from a proximal region toward the distal point. The non-linear taper defines multiple discontinuous contact regions that are circumferentially spaced about a central axis of the tool when the blades are in or near a retracted position. The contact regions are arranged to collectively center the tool relative to an implant prior to a cutting action, thereby improving alignment accuracy and reducing the risk of uneven cutting or binding.

In some aspects, each blade has a central longitudinal axis extending from a proximal end to the distal point, and each blade is configured to move through a rotational plane that is offset and non-parallel relative to the central longitudinal axis of the blade. The offset relationship between the blade axis and the plane of motion provides a displaced arcuate trajectory that increases clearance around the rim of an implant and enhances torque transmission through the cutting assembly. In other aspects, the attachment structure coupling each blade to the shaft is secured at a location offset from the blade's longitudinal axis to facilitate the displaced motion and improved cutting dynamics.

The cutting assembly may further include a translation-support structure operably engaged with the at least one shaft and one or more support arms extending between the translation-support structure and the blades. Translation of the shaft causes corresponding translation of the translation-support structure, which in turn drives rotation of the blades between the retracted and extended positions. The support arms may include proximal rotational axes that are non-intersecting with a central longitudinal axis of the shaft to reduce lateral expanse and increase structural rigidity. In some embodiments, the outermost lateral expanse of the cutting assembly is defined by diametrically opposed outer surfaces of a pair of blades to minimize incision size during insertion.

In some embodiments, each blade has a curvature generally corresponding to the outer curvature of a predetermined implant. The configuration of the cutting paths may be such that each blade traverses between approximately 25% and 50% of a tissue/bone contacting surface of the implant when transitioning between the retracted and extended positions. This proportional coverage ensures complete release of the implant with minimal rotational steps and reduced cutting time.

In another aspect, the cutting assembly includes a pair of blades, each having an inwardly curving, wedge shape with a taper extending toward a distal portion of the blade. When the blades are in or near the retracted position, each blade defines multiple spaced contact regions arranged circumferentially about a central axis of the tool. The contact regions of the pair of blades are collectively configured to center the tool relative to the implant. The pair of blades may each include non-linear tapering sides defining discrete contact regions while maintaining non-contacting arcuate segments between them. The blades move through rotational planes that are offset relative to their respective central longitudinal axes to achieve increased clearance and enhanced mechanical leverage during operation.

The features described herein may be implemented independently or in combination. The described blade geometries, offset relationships, and centering mechanisms provide improved self-alignment of the tool with the implant, greater clearance during blade movement, enhanced torque transfer, and reduced cutting force requirements, all contributing to efficient and precise implant removal.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the present invention, reference is made to the accompanying drawings, which form a part thereof, and within which are shown by way of illustration specific embodiments by which the invention may be practiced. Numerous specific details are set forth to provide a thorough description of the embodiments of the present invention. It will be apparent to one of ordinary skill in the art that some embodiments may be practiced without some of these specific details. It is to be understood that other embodiments may be utilized, and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

All numerical designations, such as measurements, efficacies, physical characteristics, forces, and other designations, including ranges, are approximations which are varied up or down by increments of 1.0 or 0.1, as appropriate. It is to be understood, even if it is not always explicitly stated that all numerical designations are preceded by the term "approximately." As used herein, "approximately" refers to being within an acceptable error range for the particular value as determined by one of ordinary skill in the art, which will depend in part on how the value is measured or determined. When an acceptable range is not dictated by the one of ordinary skill in the art, "approximately" refers to ±15% of the numerical when used in connection with particular values; it should be understood that a numerical including an associated range with a lower boundary of greater than zero must be a non-zero numerical, and the term "approximately" should be understood to include only non-zero values in such scenarios.

The phrases "in some embodiments," "according to some embodiments," "in the embodiments shown," "in other embodiments," and the like generally mean the particular feature, structure, or characteristic following the phrase is included in at least one implementation. In addition, such phrases do not necessarily refer to the same embodiments or different embodiments.

Various embodiments of the present invention provide for a wide range of technical effects, advantages, and/or improvements to implant removal tools and methods of removing implants. For the sake of brevity and clarity, the present invention is described in reference to a tool and method of removing an acetabular cup, however, embodiments of the present invention are equally applicable to removing other implants having a circular or semicircular component that may be surrounded by bone and/or tissue.

Figure 3:
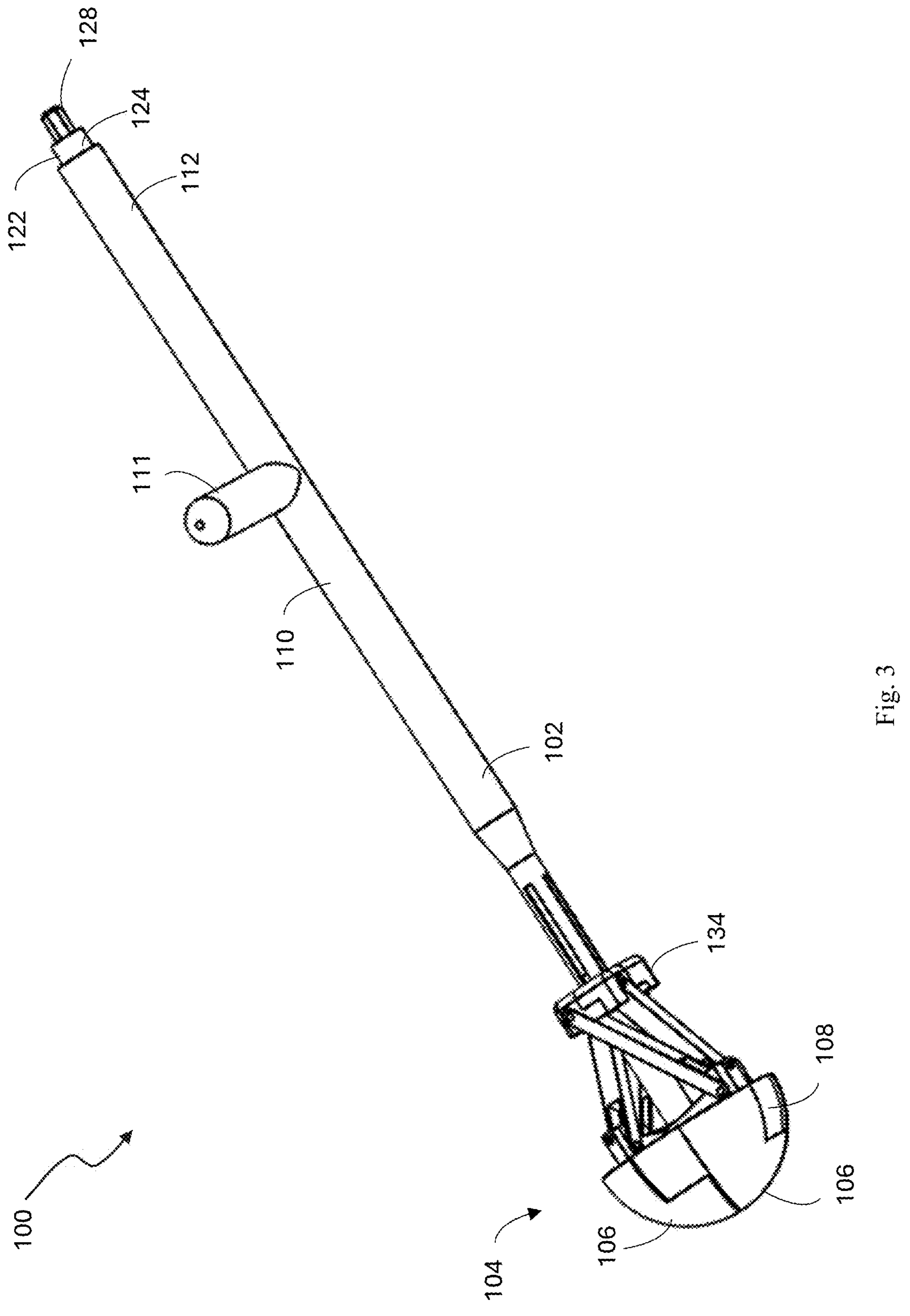
FIG. 3 is a perspective view of an embodiment of the present invention with the blades shown in a closed position around an implant. It should be noted that the blades depicted in FIG. 3 are of a different design than those depicted in FIGS. 1 and 2, but either blade design is configured to rotate between the retracted positions in FIGS. 1 and 2 to the closed position in FIG. 3.

Referring now to the figures, embodiments of the present invention include an implant removal tool 100 having an outer shaft 102 in operable communication with a cutting assembly 104. As will be explained in subsequent sections, the cutting assembly 104 includes one or more blades 106 which are configured to translate about a surface of an implant 108 as depicted in FIG. 3 to cut the implant 108 free from surrounding bone.

The outer shaft 102 has an elongated body section 110 extending between a proximal end 112 and a distal end 114. The body section may be hollow or partially hollow, thereby establishing an internal lumen 115.

The body section 110 may also include a handle such as the transversely extending handle 111. Handle 111 may extend a sufficient distance in a lateral direction to provide the operator with sufficient surface area to securely grip the implant removal tool 100. Handle 111 extends laterally to provide the operator with the ability to counteract and prevent rotation of the implant tool about its longitudinal axis during use. However, it is contemplated that the handle 111 may extend in an alternative plane or have a different shape altogether to provide an operator with a location to grip the tool 100.

The distal end 114 may have a smaller cross-sectional area relative to the proximal end 112 on account of a tapered section residing between the two ends. The reduction in cross-sectional area helps to minimize cross-sectional area of the implant removal tool 100 and thus minimize the size of the opening in the patient through which the tool 100 must pass.

The distal end 114 of the outer shaft 102 may have a round end configured to abut the rounded internal surface of the implant 108. However, alternative shapes may be employed. The distal end 114 may include an alignment structure 116. The alignment structure 116 may be permanently secured to the distal end 114. Alternatively, the alignment structure 116 may be temporarily attachable to the distal end 114 by press fitting the distal end 114 into a receipt within a surface of alignment structure 116. However, it is considered that alternative systems and methods may be employed to temporarily attach the alignment structure 116 to the distal end 114 including but not limited to a threaded attachment, snap-fit mechanism, locking tabs, cam locks, etc.

The alignment structure 116 may have a size and shape sufficient to fit within an acetabular cup implant 108. In some embodiments, the alignment structure 116 is a semi-circular design to match that of the acetabular cup implant 108. Moreover, the present invention may include a plurality of alignment structures 116 sold as a kit with each alignment structure 116 having a particular size and shape to match that of various different acetabular cup implants 108, such as, acetabular cups with internal diameters of 28 mm, 32 mm, 36 mm, and 40 mm. As a result, the present invention can be used to remove acetabular cup implants 108 of different sizes.

In some embodiments, a portion of the body section 110 includes one or more slots or channels 118 extending through the body section 110 to provide access to the internal lumen 115 of the outer shaft 102. Slots 118 may be located proximate to the distal end 114 to reduce the length of the cutting assembly 104.

As depicted in the exemplary embodiment, tool 100 has four slots 118 that are equidistantly spaced about the circumference of the body section 110. However, more or less slots 118 may be employed. Moreover, the circumferential spacing of the slots 118 ensures more balanced force distribution, but alternative spacing may be employed.

Each slot 118 has a width sufficient to allow passage of at least a portion of the cutting assembly 104 as will be explained in subsequent sections. In addition, each slot 118 has a length extending parallel to the longitudinal axis of the outer shaft 102. The length is sufficient such that at least a portion of the cutting assembly can translate a sufficient distance to move the blades 106 between an open and a closed configuration. This functionality will be explained in subsequent sections.

In some embodiments, the body section 110 of the outer shaft 102 includes a helical thread 119 on an internal surface of the outer shaft 102 that forms the internal lumen 115. The helical thread 119 may have a longitudinal expanse that is equal to or greater than the distance that the internal shaft 122 needs to move in a longitudinal direction to move the blades 106 from an open configuration to a closed configuration. Again, this functionality will be explained in subsequent sections.

Figure 1:
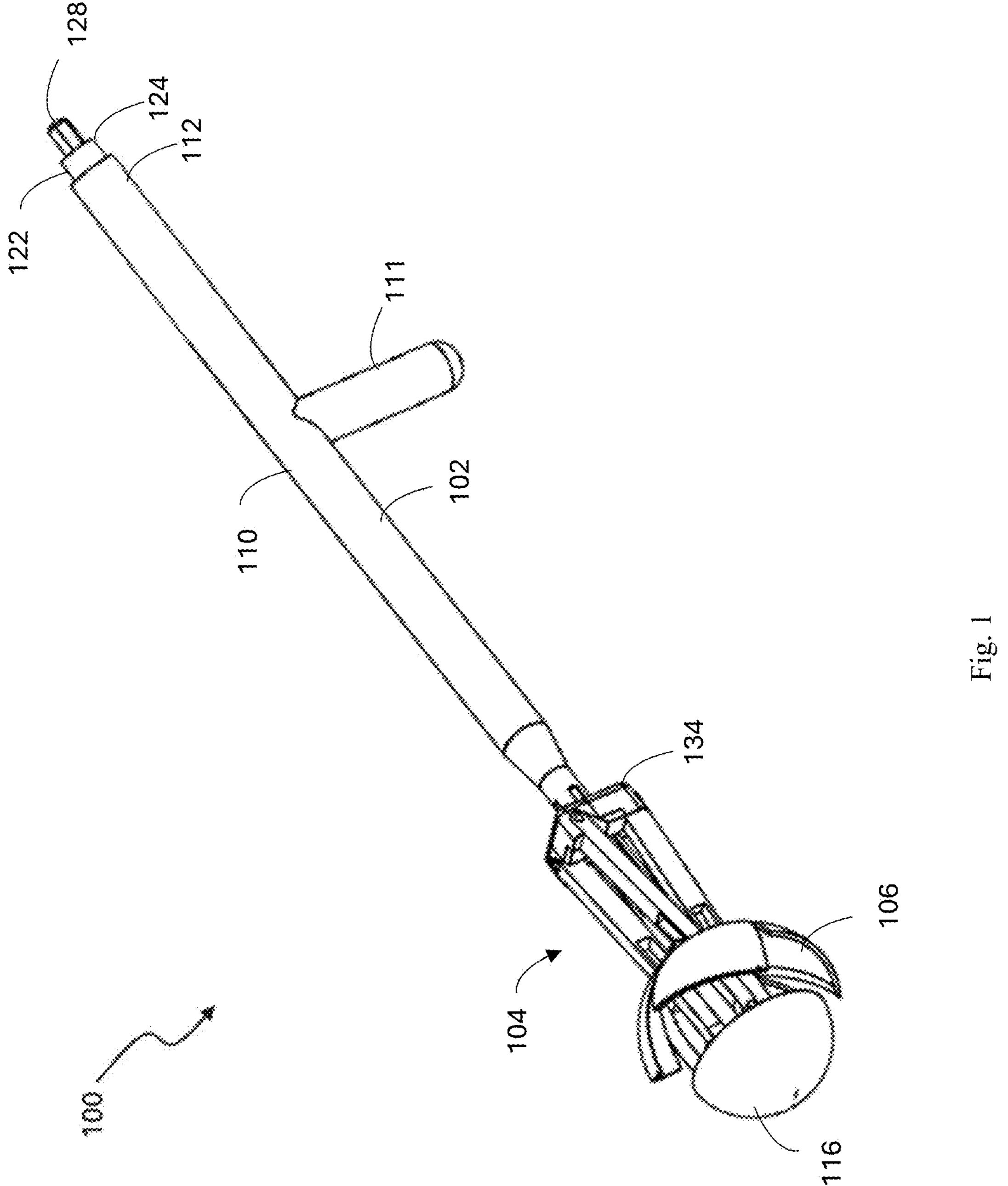
FIG. 1 is a perspective view of an embodiment of the present invention.
Figures 4, 5:
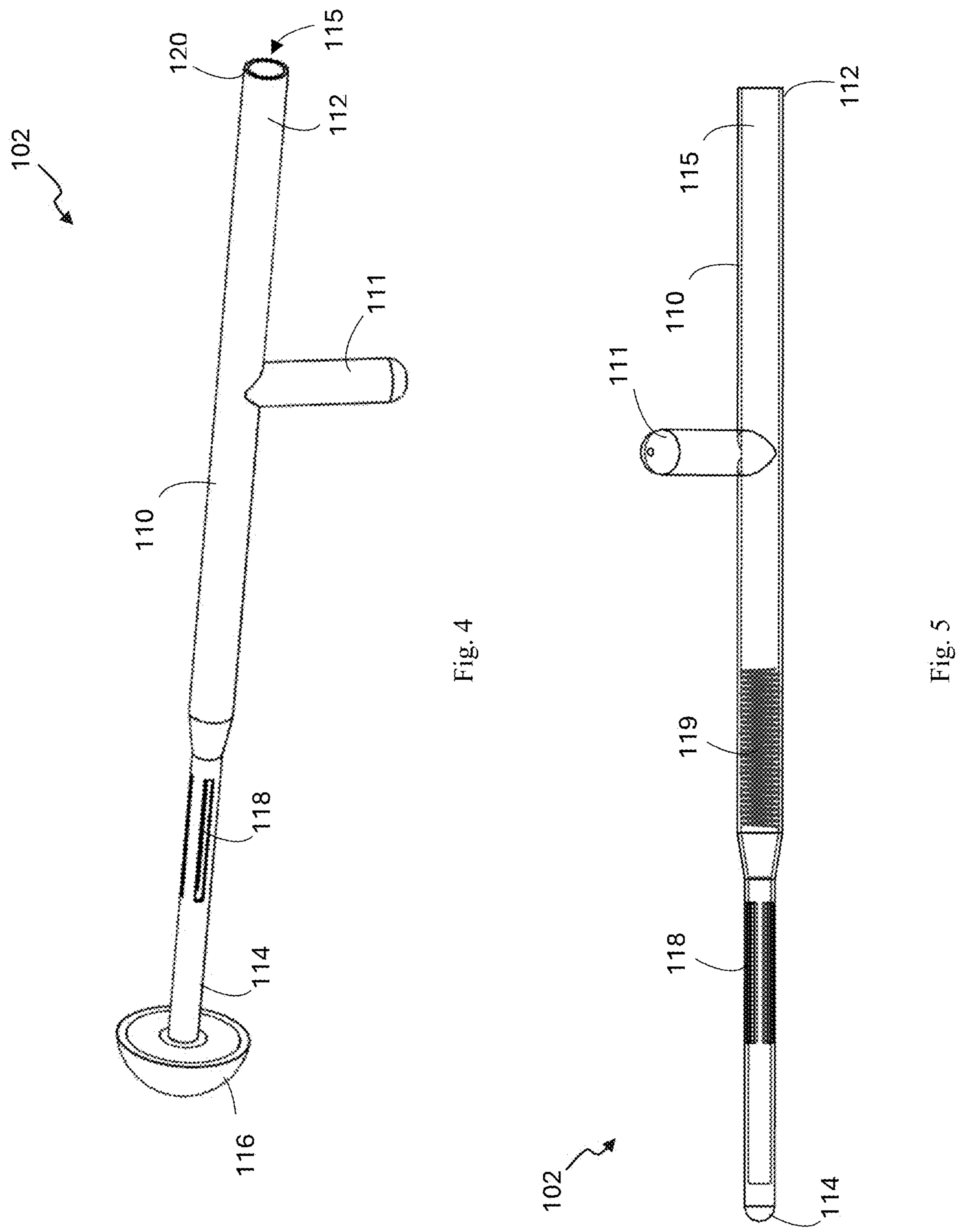
FIG. 4 is a perspective view of an embodiment of the outer shaft with an alignment guide secured to the distal end.
FIG. 5 depicts an embodiment of the outer shaft in a transparent view to show the internal features of the structure.

As best depicted in FIGS. 4-5, the proximal end 112 of the outer shaft 102 includes an opening 120 extending to the internal lumen 115 of the outer shaft 102. The opening 120 is sufficiently sized to receive an internal shaft 122 as depicted in FIGS. 1 and 3. The internal shaft 122 thus has a size and shape to pass through the opening 120 and reside within the internal lumen 115 in the outer shaft 102.

Figure 6:
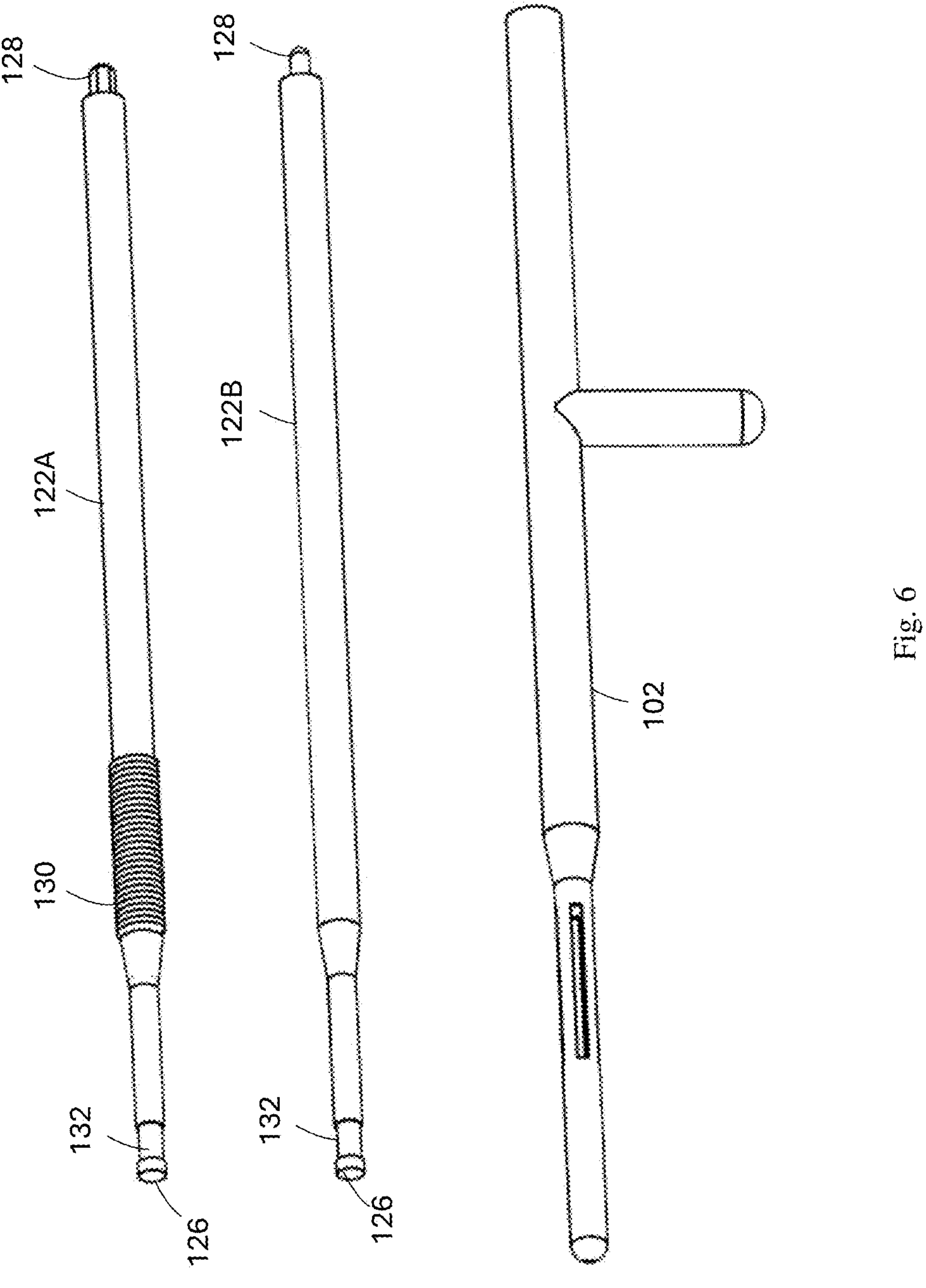
FIG. 6 is a perspective view of an embodiment of the outer shaft with two different embodiments of the internal shaft.
Figure 7:
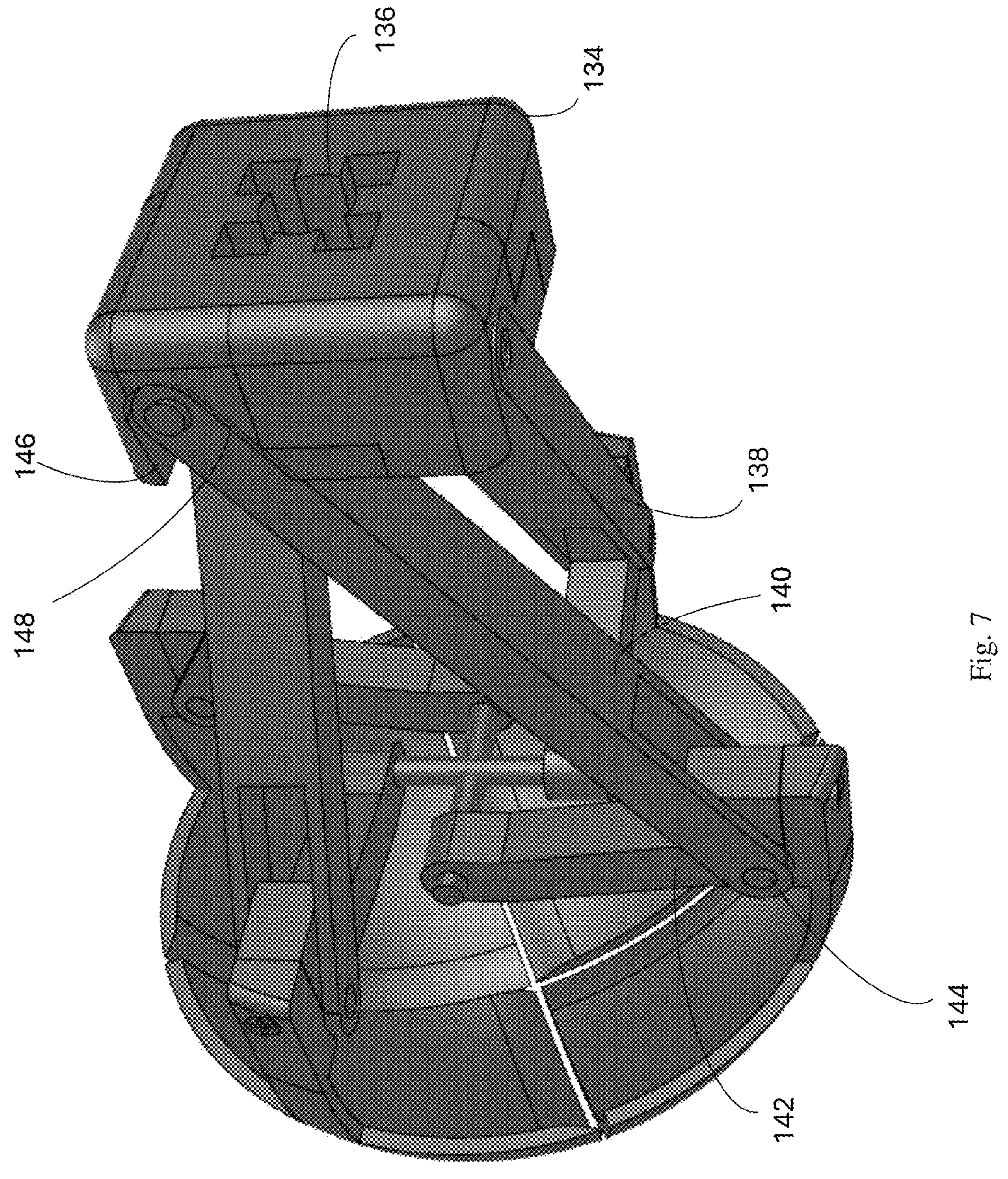
FIG. 7 is a close up rear perspective view of an embodiment of the cutting assembly.

In some embodiments, the internal shaft 122 has a length that is less than the length of outer shaft 102, yet longer than a distance between the proximal end 112 and the distal end of the slots 118 on outer shaft 102, as illustrated in FIG. 6. This length ensures that a proximal end 124 of the internal shaft 122 extends proximally beyond the proximal end 112 of outer shaft 102 even when the distal end 126 extends distally beyond the slots 118. The length of the internal shaft 122 is such that at least a portion of the proximal end 124 is accessible by a user of tool 100.

As provided in FIG. 6, some embodiments of the internal shaft 122, such as internal shaft 122A, include a shank 128 configured to operably engage a surgical tool, such as a drill, located at the proximal end 124. While the depicted shank 128 on internal shaft 122A is a hex shank, alternative shank designs are considered including but not limited to straight shanks, quick-change shanks, tri-flatted shanks, tapered shanks, Morse taper shanks, threaded shanks, snap-lock or bayonet shanks, slotted shanks, spline shanks, notched shanks, D-shaped shanks, cross-pin shanks, and collet shanks.

Some embodiments of the internal shaft 122, such as internal shaft 122B in FIG. 6, are configured to operably engage a hammer drill or a be struck by a manual hammer. Thus, the proximal end 124 of the internal shaft 122 may lack the hexagonal cross-sectional shape and instead provide a generally flat striking surface or include a shank configured to be struck by a hammer. In addition, embodiments of the present invention may include a kit having both a translational internal shaft 122B and a rotational internal shaft 122A.

As illustrated on the internal shaft 122A, the body section of the internal shaft 122A may include a helical thread 130 that is configured to operably engage the helical thread 119 in the lumen 115 of the external shaft 102. Thus, a user can connect a rotational drill to the shank 128 to rotate the internal shaft 122A relative to the outer shaft 102 to engage the threads 119 and 130. Rotation in a first direction causes the internal shaft 122A to move in a distal direction relative to the outer shaft 102 and rotation in an opposite, second direction causes the internal shaft 122A to move in a proximal direction relative to the outer shaft 102.

In some embodiments, as depicted in FIG. 6, the body section of the internal shaft 122B is devoid of a helical thread. Likewise, the internal lumen 115 of the external shaft 102 may also be devoid of a helical thread or there may be sufficient clearance such that the thread 119 does not restrict translation of the internal shaft 122B. As a result, the operator can use a hammer, hammer drill, or any other percussion device to deliver a force to the proximal end of the internal shaft 122B thereby causing the internal shaft 122B to move in a distal direction relative to the outer shaft 102.

The distal end 126 of the internal shaft 122 is configured to operably engage the cutting assembly 104. In some embodiments, the distal end 126 of the internal shaft 122 includes a cylindrical stem 132 that functions as an attachment point for cutting assembly 104. The cylindrical stem 132 may have a reduced diameter or may be bordered by adjacent sections having larger diameters to provide structural shoulders, which aid in retaining the cutting assembly 104 to the cylindrical stem 132.

As noted above, the cutting assembly 104 is configured to operably engage the implant removal tool 100. In some embodiments, the cutting assembly 104 engages the internal shaft 122. As a result, longitudinal movement of the internal shaft 122 causes translation of the cutting assembly 104, which is visually illustrated in comparing FIG. 8 to FIG. 10.

In some embodiments, this engagement occurs through the translation-support structure 134. As best depicted in FIGS. 7-10, the translation-support structure 134 includes inwardly extending retention members 136 that pass through slots 118 and abut the stem 132 between the bordering structural shoulders. In some embodiments, the inwardly extending retention members 136 form a cylindrical opening or a discontinuous cylindrical opening that extends through the translation-support structure 134. In some embodiments, the inwardly extending retention members 136 form a non-cylindrical opening that is configured to abut a non-circular cross-sectional shape of the outer surface of the stem 132. It is considered that alternative methods and devices can be used to form an operable engagement between the translation-support structure 134 and the internal shaft 122.

The translation-support structure 134 also provides a structural support to which one or more articulating support arms 138 is attached. The one or more support arms 138 extends to one or more blades 106. Thus, movement of the translation-support structure 134, resulting from translation of the internal shaft 122, transfers forces through the support arms 138 in turn causes movement of the blades 106.

Figure 16:
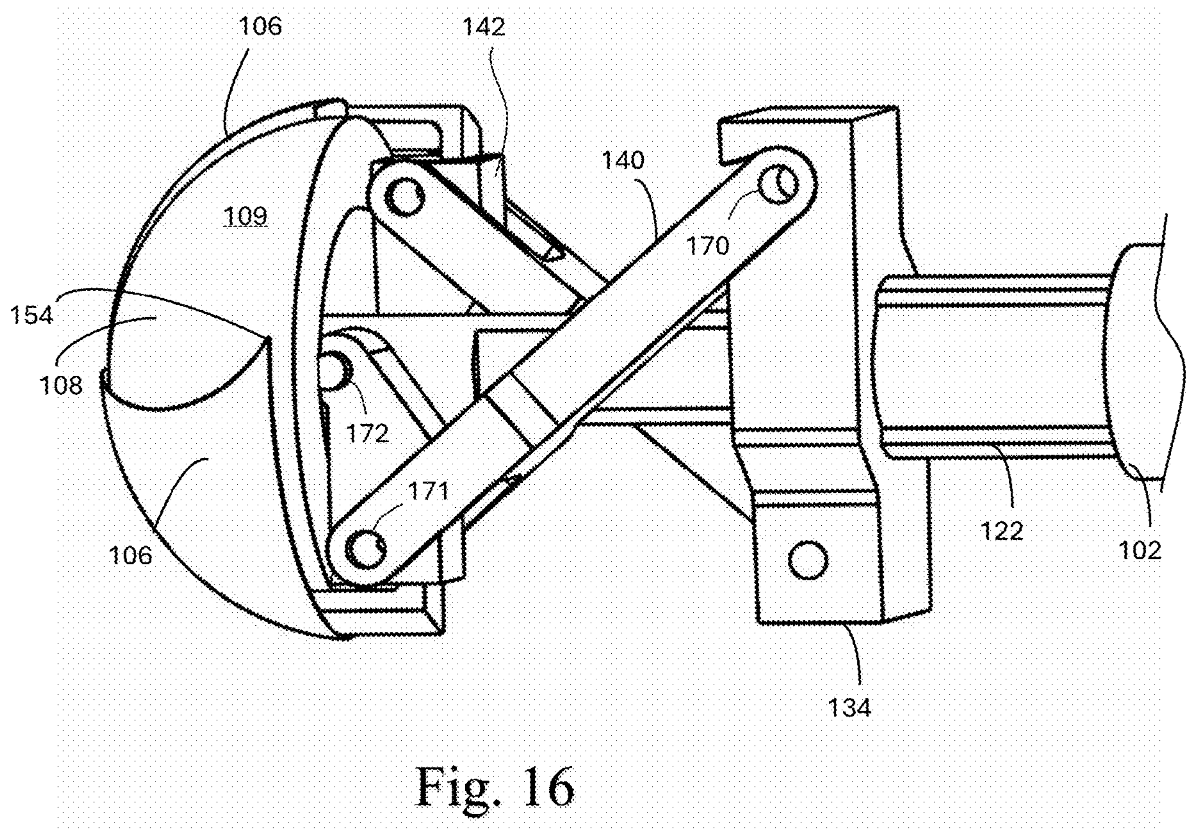
FIG. 16 is a close up perspective view of a distal end of an embodiment of the present invention with the blades in an extended position, illustrating pivot axes 170 and 171 and proximal rotational axis 172 of the support-arm linkage.

In some embodiments, there is a single support arm extending between the translation-support structure 134 and each blade 106. However, it is contemplated that more than one arm segment may extend between the translation-support structure 134 and each blade 106. In some embodiments, a first arm segment 140 is operably attached to the translation-support structure 134 at one end and is operably attached to a second arm segment 142 at a pivot joint 144, the pivot joint 144 defining a pivot axis 171 (see FIG. 16).

The second arm segment 142 extends back towards and pivotably attaches to the outer shaft 102. It should be noted that while the outer shaft 102 is not depicted in FIG. 7 to better depict the components of the cutting assembly 104, the connection between the second arm segment 142 and the outer shaft is depicted in FIGS. 9-10.

In some embodiments, the first arm segment 140 is pivotably attached to the translation-support structure 134 about a pivot axis 170 (see FIG. 16) in a restricted manner. For example, the translation-support structure 134 may include rotational stops 146 and 148 (see FIG. 7) to ensure that the first arm segment 140 is constrained within a predetermined range of rotation.

Figure 9:
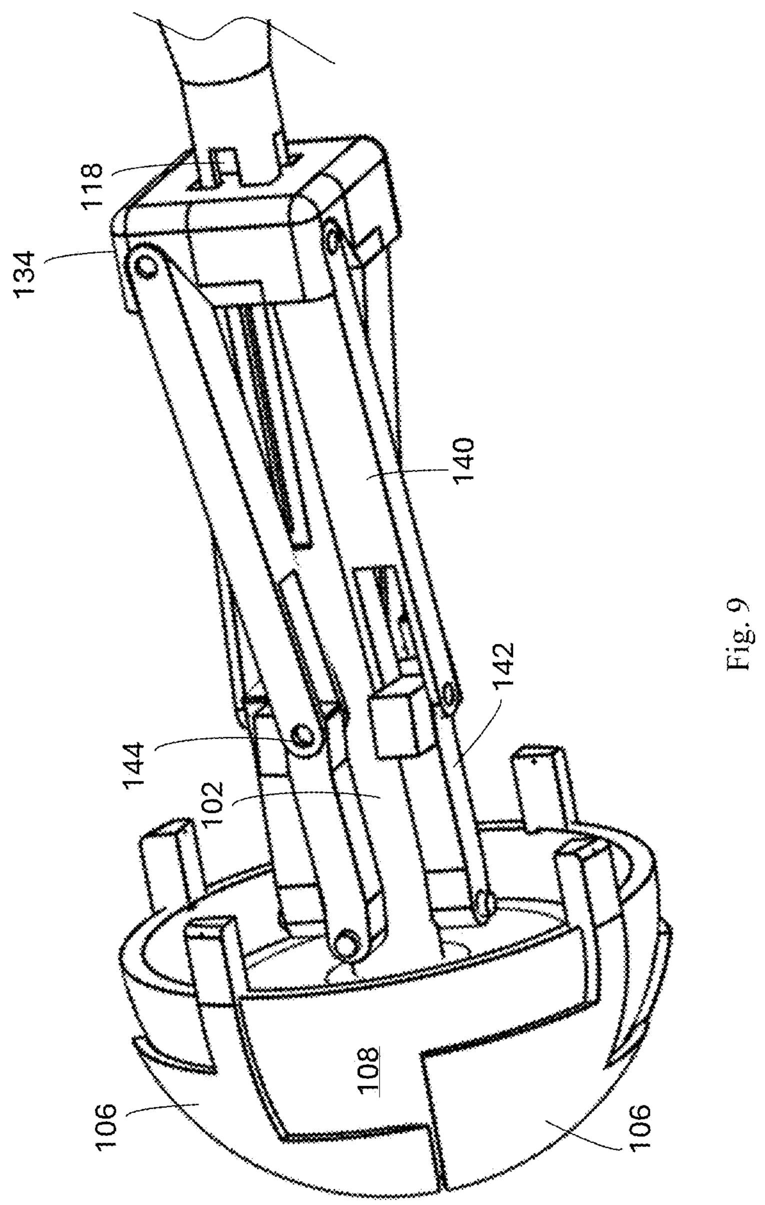
FIG. 9 is a close up perspective view of a distal end of an embodiment of the present invention with the blades detached from the cutting assembly when the cutting assembly is in a retracted position.
Figure 10:
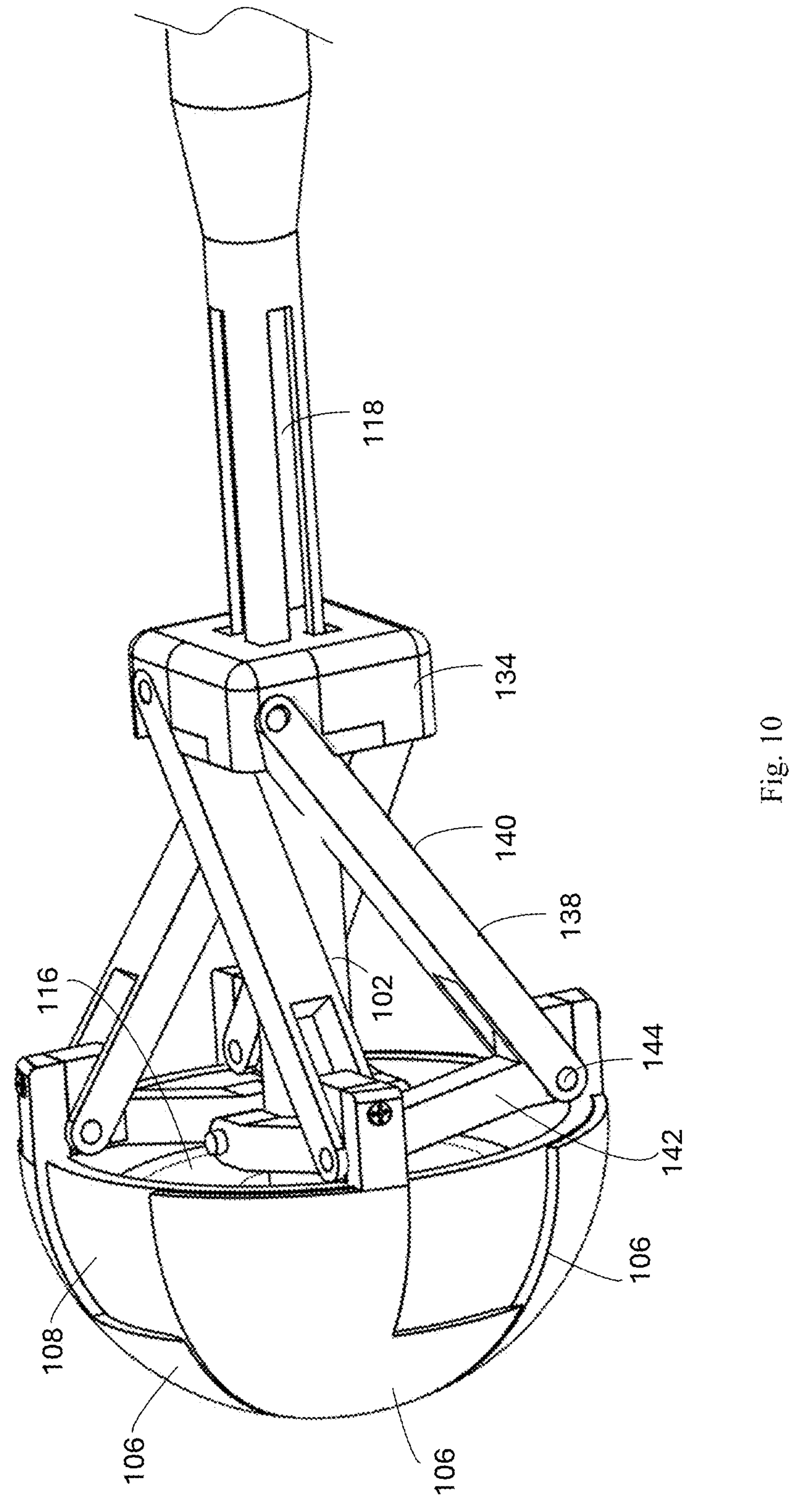
FIG. 10 is a close up perspective view of a distal end of an embodiment of the present invention with the blades in a closed position.

As best depicted in FIGS. 9-10, the first and second arm segments 140 and 142 are laterally and radially offset from the central longitudinal axis of the outer shaft 102. The offset configuration aids in reducing the overall cross-sectional expanse of tool 100 to minimize the size of the incision necessary to insert the tool 100 and reduce the risk of unintentional interaction with surrounding tissue. Moreover, each of the arm segments 140 and 142 resides within the lateral expanse extending between diametrically opposed blades 106.

The depicted embodiment includes four articulating support arms 138 (the combination of the first and second arm segments 140 and 142) that attach to four blades 106. It is contemplated that alternative embodiments may employ more or less articulating support arms 138, arm segments 140 and 142, and/or blades 106.

Figure 8:
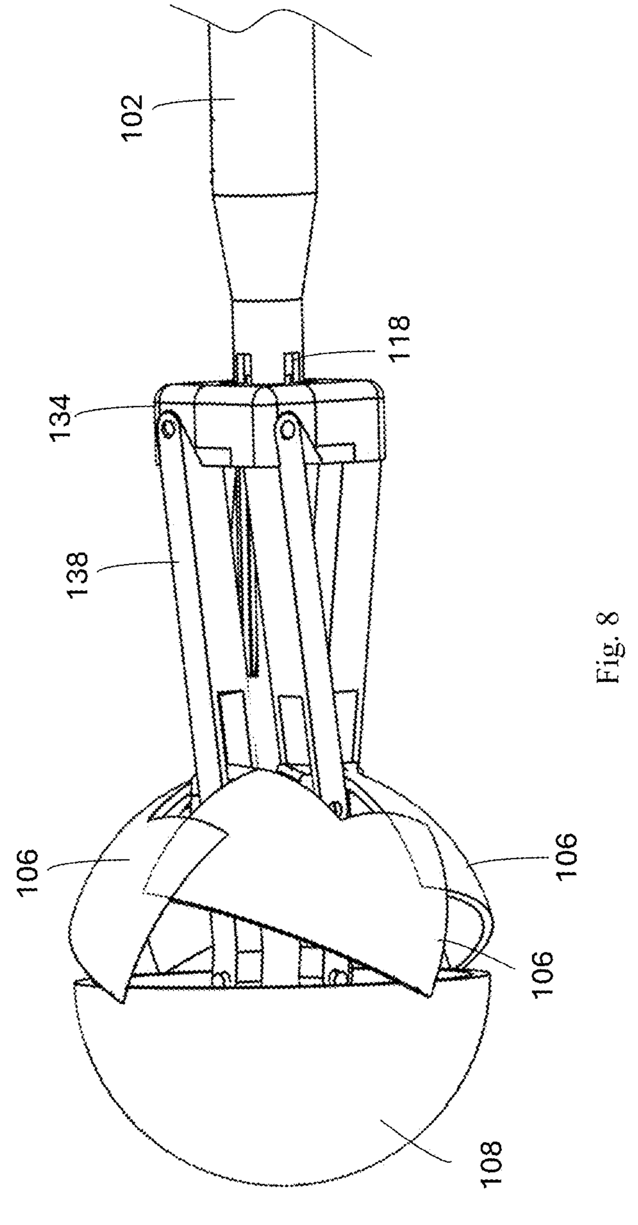
FIG. 8 is a close up side view of a distal end of an embodiment of the present invention with the blades in a retracted position while the tool is aligned with an implant.

Each blade 106 is attached to one of the articulating support arms 138. It should be noted that while FIGS. 8 and 10 show this attachment, FIG. 9 shows the blades detached to clarify the structure and movement of the first and second arm segments 140 and 142. In some embodiments, each blade 106 is secured to a proximal end of the second arm segment 142 in a non-rotational, fixed manner. Thus, movement of the second arm segment 142 causes movement of the attached blade 106. As constructed in the depicted embodiment, the second arm segment 142 pivots about the attachment to the outer shaft 102 about a proximal rotational axis 172 (see FIG. 16), which in turn moves the attached blade 106 in a semi-circular arc.

Referring now to FIGS. 11-14, each blade 106 has an inwardly curving wedge shape that tapers to a sharp point 150 when moving in a generally distal direction from its respective attachment structure 151. Each blade 106 includes the wedge like shape to reduce friction during the "stab-like" cutting path as the blade 106 moves in an arcuate, distal direction.

The inwardly curve of each blade 106 mirrors the curvature of an outer surface of a predetermined implant 108. For example, the outer diameters of acetabular cups commonly range between 48-60 mm with the mean size falling between 52 mm and 55 mm. Thus, each blade 106 can have a curvature that corresponds to one or more of these size ranges. In addition, some embodiment of the present invention include a plurality of interchangeable blades 106 so that the properly sized blades 106 can be used for a particular implant 108.

Each blade 106 may also include a sharpened side 162 leading to the sharp point 150. In some embodiments, both sides leading to the sharpened point 150 are sharpened to cut bone. In addition to aiding in cutting bone, the sharpened side 162 allows the side of a blade 106 to slide overtop (or below in some embodiments) an adjacent blade 106 when the blades 106 are moved into their retracted positions as shown in FIGS. 2 and 8.

Figure 11:
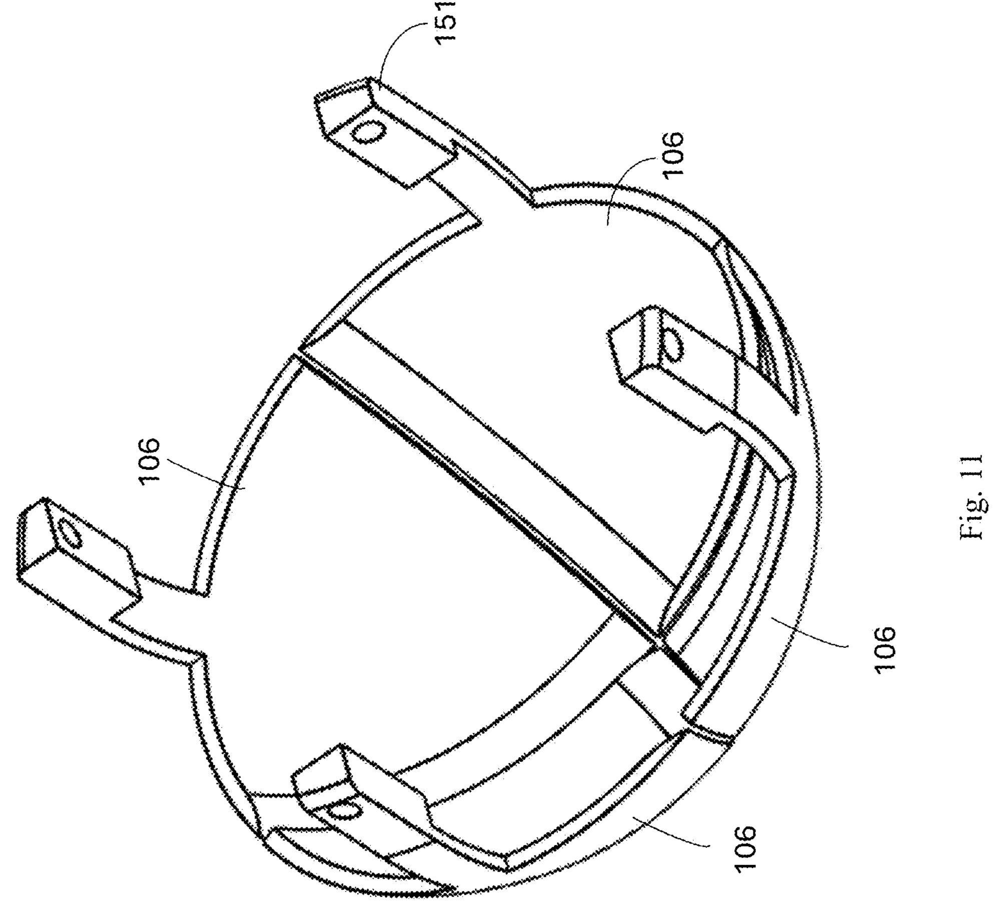
FIG. 11 is a perspective view of an embodiment of the blades in a closed position.
Figure 13:
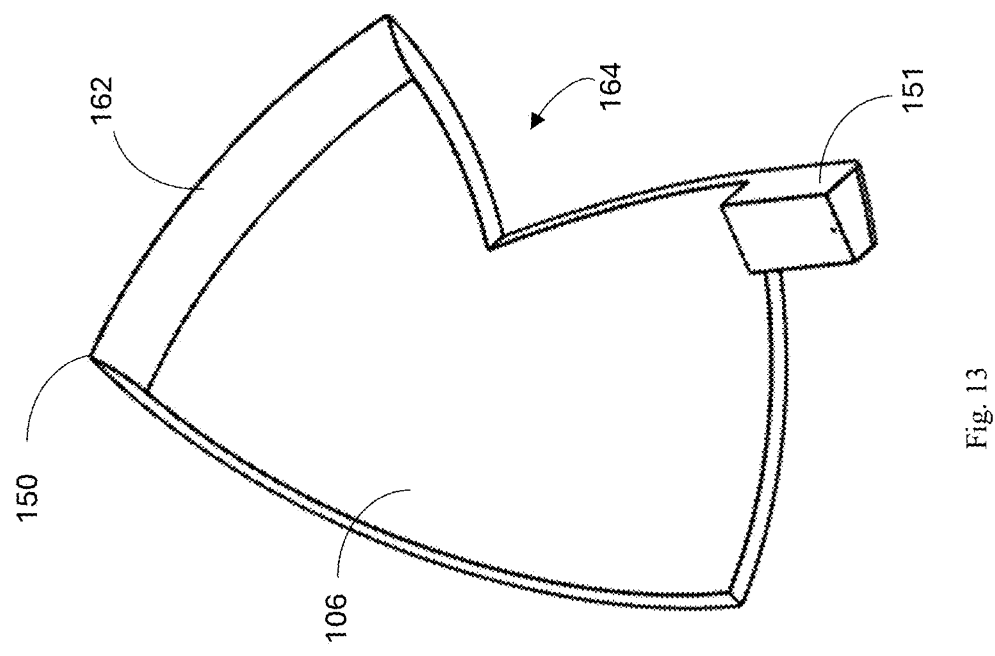
FIG. 13 is an internal view of an embodiment of a blade.
Figure 12:
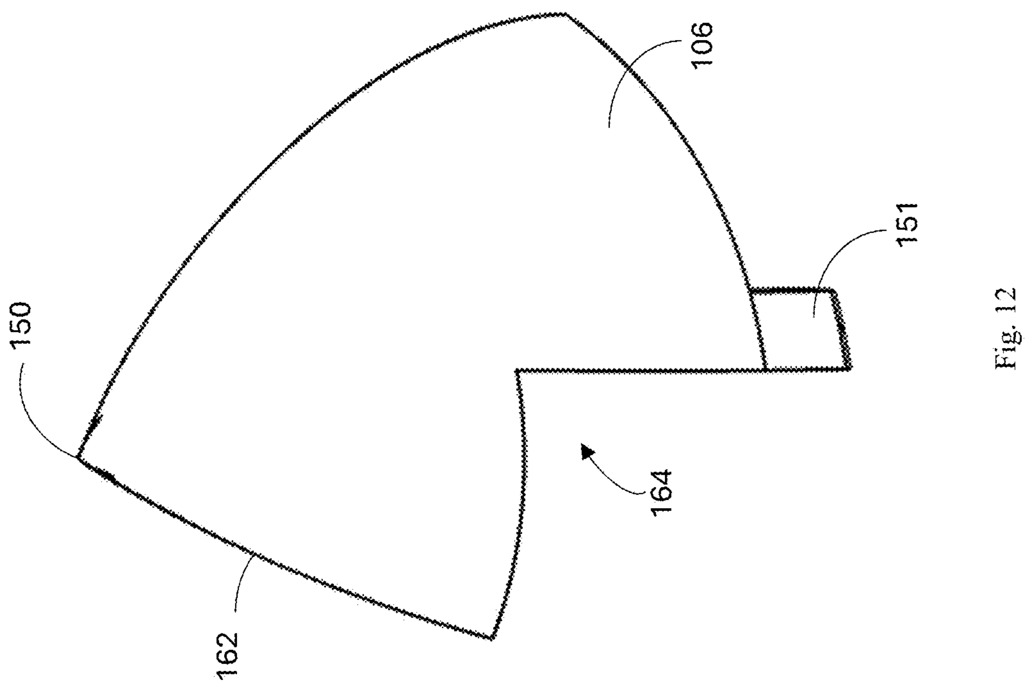
FIG. 12 is an external view of an embodiment of a blade.
Figure 14:
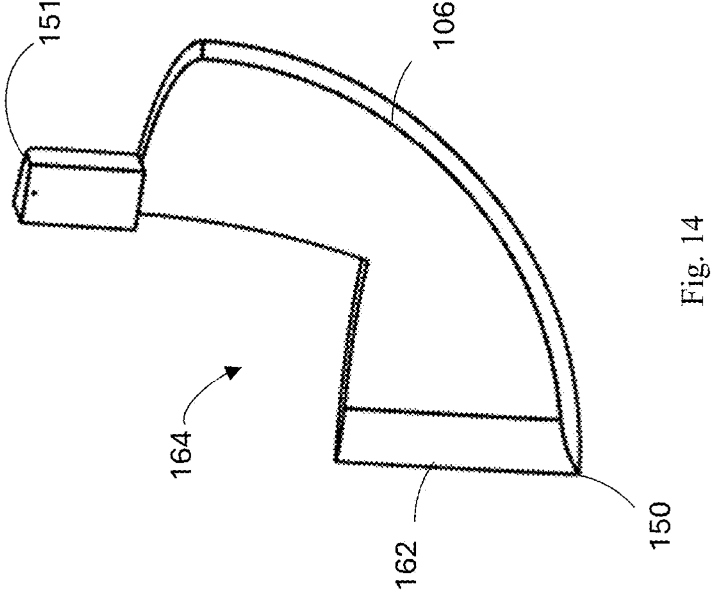
FIG. 14 is an internal perspective view of an embodiment of a blade.

As depicted in FIGS. 12-14, in some embodiments, each blade 106 also includes a cutout, such as the L-shaped cutout 164. The cutouts 164 provide a receiving space through which one or more arm segments 140 and 142 can reside when the blades 106 are moved into their retracted positions. However, some embodiments of the blades 106 do not include the cutouts 164 and instead have an elongated extension to attachment structure 151 as depicted in FIG. 11.

Figure 2:
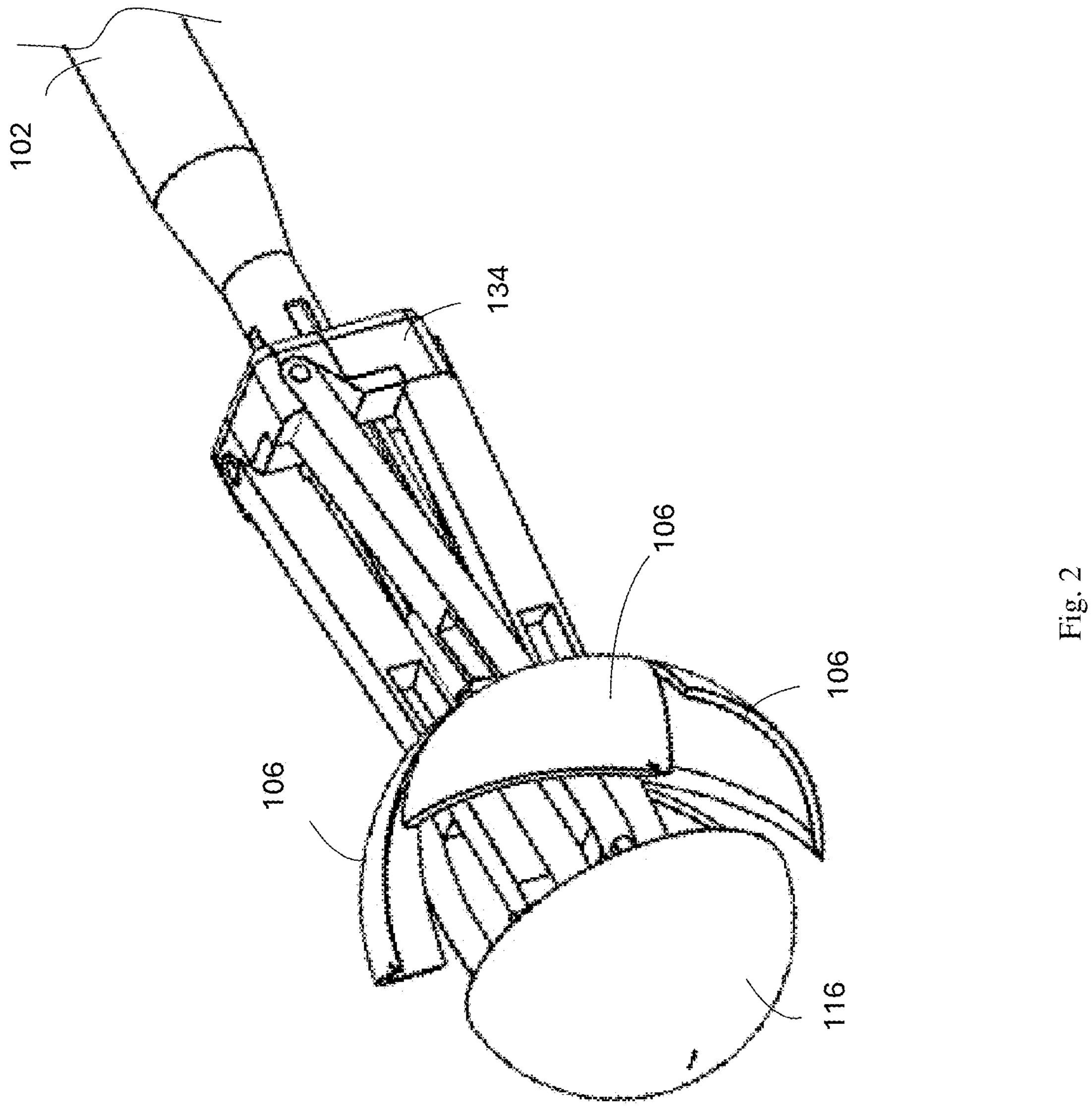
FIG. 2 is a close up view of an embodiment of the present invention while the blades are in a retracted position.

In some embodiments, cutting assembly 104 includes a multitude of blades 106 that rotate from their retracted positions in FIGS. 1, 2, and 8 to their closed positions as shown in FIGS. 3 and 10. When in the closed position (also referred to as "the fully extended position"), the blades 106 come together to fully enclose the outer surface of the implant 108. In moving from the retracted position to the closed position, the blades 106 transition along the outer surface of the implant 108 and cut the surrounding bone from the outer surface of the implant 108. Upon reaching the closed position, the implant 108 is free from the surrounding bone and the tool 100 can be removed with the implant 108 residing within the closed blades 106.

While four blades 106 are depicted in the illustrated embodiment, it is considered that more or less blades 106 can be used to plunge through the surrounding bone to reach a closed position in which the blades 106 have freed the entire outer surface of the implant 108 from the surrounding bone. Some embodiments have two or more blades 106. Some embodiments have three or more blades 106, and some embodiments have two to eight blades 106.

For example, FIGS. 15-20 depict an embodiment having two blades 106. In this embodiment, each blade 106 is configured to rotate about the implant 108 to cut a portion of the tissue/bone surrounding the implant 108. The use of two blades 106 may provide several advantages, such as reducing the overall size of the cutting assembly 104, minimizing the incision size required for insertion of the tool 100, and simplifying the mechanical linkage required to actuate the blades. However, it is also contemplated that more or fewer blades 106 may be employed depending on the particular surgical requirements, implant geometry, and desired cutting efficiency.

Figure 17:
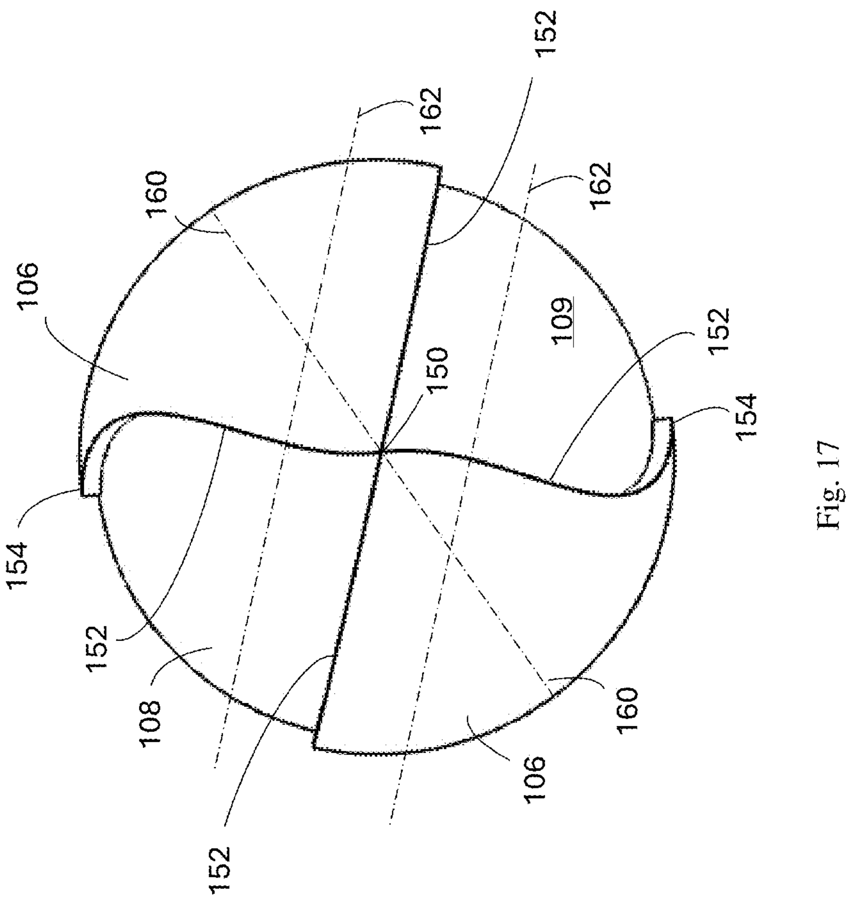
FIG. 17 is an end view of an embodiment of the present invention with the blades in an extended position around an implant.
Figure 18:
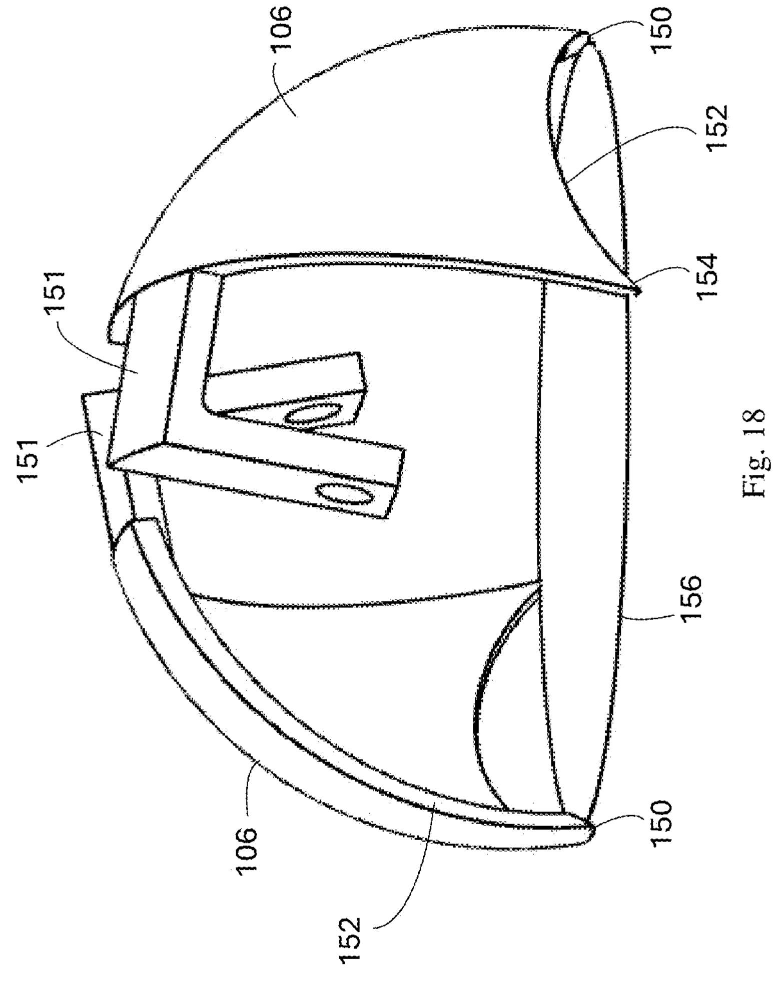
FIG. 18 is a perspective view depicting a pair of blades in a retracted position in accordance with some embodiments of the present invention with the rest of the tool removed to aid in visualizing the contact regions of the blades.

As depicted in FIG. 17, the blade size and a resulting single cutting path of each blade may traverse approximately 25% of the tissue/bone contacting surface 109 of the implant 108. In some embodiments, the blade size and a resulting single cutting path of each blade may traverse more than 25% but less than 50% of the tissue/bone contacting surface 109 of the implant 108. While the dimensions, ratios, and coverage percentages described herein are provided in connection with some embodiments, it should be understood that the blade size, curvature, and cutting path may be more or less than the explicit values disclosed, depending on the particular application, implant size, or surgeon preference.

For example, smaller blades may be beneficial when operating in confined anatomical spaces or when removing implants that require more localized cutting. Larger blades, on the other hand, may be advantageous for removing larger implants or when faster removal is desired, as they can traverse a greater portion of the implant's outer surface in a single cutting motion. The overall size, curvature, and cutting angle of the blades 106 may thus be selected or adjusted based on implant dimensions, bone density, and the surgeon's preferred technique. Interchangeable blade configurations may also be provided to allow the same implant removal tool 100 to accommodate a range of implant sizes and surgical applications.

For the two blade design, the implant removal tool 100 is configured to traverse the entire tissue/bone contacting surface 109 of the implant 108 by aligning the tool with the implant 108 in a first orientation, executing a cutting action, retracting the blades, rotating the tool approximately 90 degrees about the longitudinal axis of the tool, and then executing a second cutting action. When an alternative number of blades are used or blades of an alternative size are used, the tool may need to be rotated more than once and additional cuts may be required to ensure that the blades traverse the entire tissue/bone contacting surface 109 of the implant 108.

As will be explained in greater detail herein, in some embodiments, the blade design and/or the orientation of the blades 106 when in their retracted or near retracted positions includes one or more points/regions surrounding, and in some cases contacting, the implant 108. These points/regions ensure that the tool 100 is centered about the implant 108 prior to initiating a cutting action to reduce the likelihood of binding the blades on the tissue/bone contacting surface 109 of implant 108. It should be noted that the contact points/regions described herein may occur along a single blade 106 or may collectively result from multiple blades 106 arranged circumferentially about the implant 108.

In some aspects, the blades 106 may include a tapered shape with one or more of the lateral, tapering sides 152 having a non-linear taper moving in a proximal-to-distal direction. In reference to the proximal-to-distal direction, the proximal end of each blade 106 is the side from which the attachment structure 151 extends and the distal end of each blade 106 is established by the distal point 150. In this manner, the non-linear taper extends between a lateral point 154 and the distal point 150.

Figure 15:
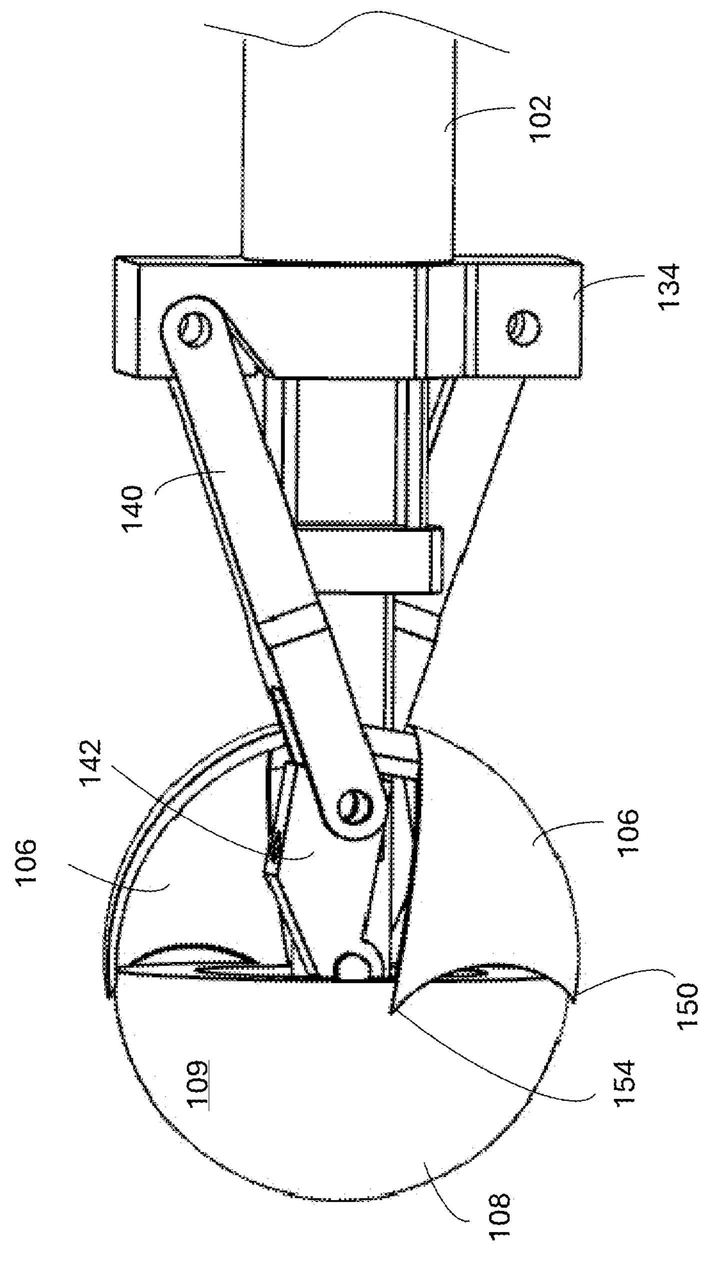
FIG. 15 is a close up perspective view of a distal end of an embodiment of the present invention with the blades in a retracted position.

The non-linear taper produces multiple discontinuous contact points/regions with the implant 108 when the blades 106 reside in a retracted position or close to the fully retracted position as exemplified in FIG. 15. The contact points/regions may include the lateral point 154 and/or the distal point 150. These contact points/regions collectively surround at least a portion of the implant 108 when the blades 106 reside in a retracted position or close to the fully retracted position, which ensure that the tool 100 is centered about the implant 108 prior to initiating a cutting action.

In some aspects, at least one of the lateral, tapering sides 152 of the blades 106 is shaped such that, when the blades 106 are in the retracted position, a radial plane 156 extending through the contact points/regions will intersect at least two points on a single blade 106, while a majority of the circumferential expanse of the radial plane 156 extending between the contact points/regions is non-intersecting with that particular blade 106. In some aspects, the non-linear taper may be established by an arcuate shape defining two or more discrete contact points/regions in a circumferential expanse about the implant 108 when the blades are in or near their retracted position. Put another way, the non-linear taper defines two or more contact points/regions for a single blade 106 that extend distally beyond other portions of said blade 106 when said blade 106 is in or near the retracted position. This configuration is exemplified in FIG. 15 which depicts both the lateral point 154 and the distal point 150 surrounding and contacting the implant 108 with an arc extending between the two points to ensure that a majority of the blade is in non-contacting relation with the implant 108 when the blade is in or near the retracted position.

In some aspects, the non-linear taper ensures that a majority of the lateral, non-linear tapering sides 152 of the blades 106 do not surround or come in contact with the implant 108 and/or the tissue/bone surrounding the implant 108 when the blades are in or near the retracted position. As such, less force is required to initially seat and center the tool 100 about the implant 108.

The non-linear taper may also be configured to shape the contact points/regions into sharpened points. The sharpened contact points/regions aid in penetrating the tissue/bone surrounding the implant 108 when initially seating and centering the tool 100 about the implant 108. The result is again a reduction in force required to initially seat and center the tool 100 about the implant 108.

In some embodiments, the implant removal tool 100 and/or each blade 106 may be configured such that, when the blades 106 are in or near the retracted position, the blades establish two or more discrete and circumferentially spaced contact points/regions with the tissue/bone contacting surface 109 of the implant 108. These discrete contact points/regions assist in centering the tool 100 relative to the implant 108 prior to performing a cutting motion, thereby improving alignment accuracy and reducing the risk of uneven cutting or binding the blades on the tissue/bone contacting surface 109. In other embodiments, the tool 100 and/or each blade 106 may be designed such that three or more discrete and circumferentially spaced contact points/regions are formed when the blades 106 are in or near the retracted position. The presence of three or more contact points/regions may further enhance stability and centering accuracy, particularly when the implant 108 exhibits surface irregularities or when the bone interface is uneven. This multi-point contact configuration allows the tool 100 to achieve self-centering alignment without requiring excessive manual adjustment by the surgeon, facilitating more consistent and predictable cutting performance.

Figure 20:
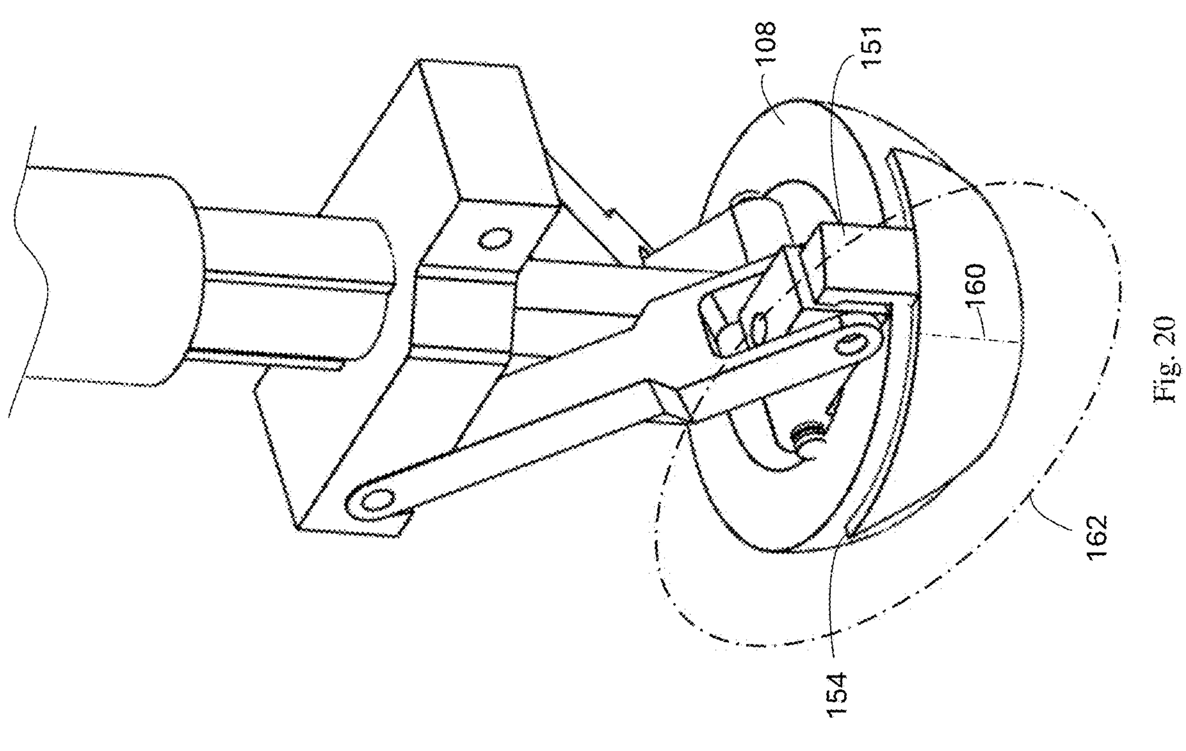
FIG. 20 is a close up perspective view of a distal end of an embodiment of the present invention with the blades in an extended position.
Figure 19:
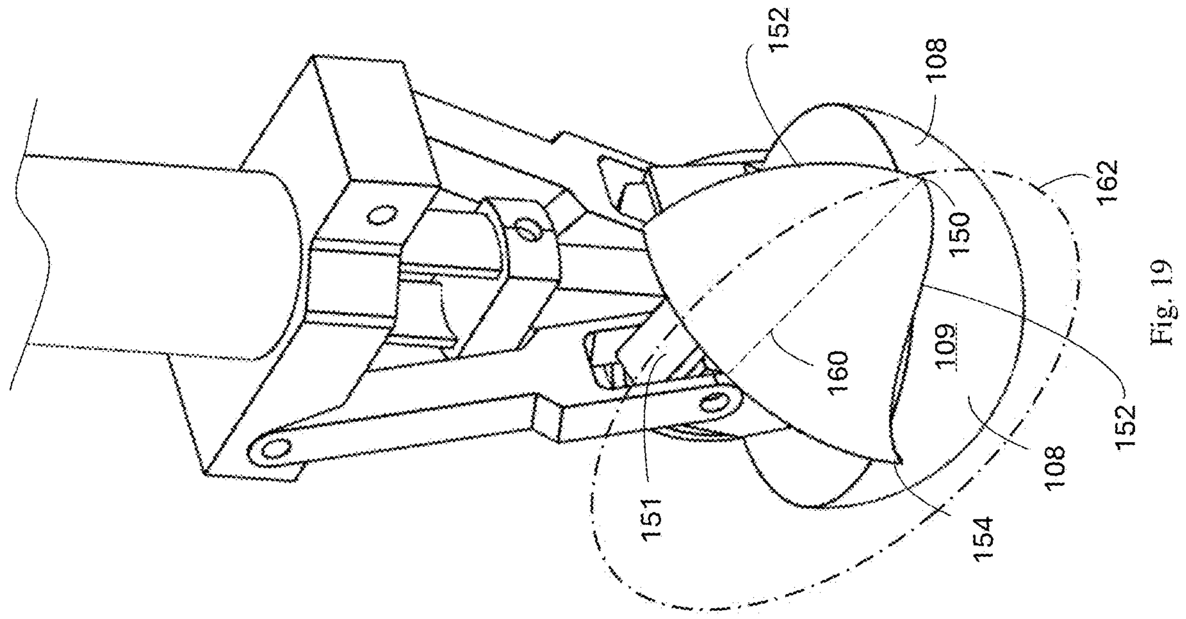
FIG. 19 is a close up perspective view of a distal end of an embodiment of the present invention with the blades in a retracted position.

In some aspects, as depicted in FIGS. 19-20, the attachment structure 151 on each blade 106 may be offset relative to the circumferential center point about the proximal end of the blade 106. In some embodiments, the attachment structure 151 on each blade 106 may be offset relative to the central longitudinal axis 160 of the corresponding blade 106. In some embodiments, the central longitudinal axis 160 is laterally and radially offset and/or non-parallel to the moment arm about which the blade 106 is rotated. In some aspects, each blade 106 is configured such that its central longitudinal axis 160 is laterally and radially offset and/or non-parallel with respect to a plane/cutting trajectory 162 (also referred to as a "rotational plane") through which the blade 106, and in some cases its attachment structure 151, move during rotation between the retracted and extended positions. The offset and angular displacement between the central longitudinal axis 160 may also be offset relative to the central longitudinal axis of the tool 100.

This offset orientation alters the blade's cutting trajectory such that the arcuate cutting path more closely conforms to the curvature of the implant 108 while simultaneously providing increased clearance around the implant rim. The offset between the blade axis 160 and its rotational axis 162 and/or the longitudinal axis of the tool 100 also increases mechanical leverage during rotation, thereby enhancing torque transfer and rigidity through the arm segments. Moreover, the extent of the offset may be such that the lateral point 154 is positioned in a more distal direction relative to the opposite lateral point 158 of the blade 106 such that the lateral point 154 may function as a one of the implant contacting points when the blade 106 is in or near the retracted position.

Another result of the offset nature of the attachment structure 151 is that the lateral point 154, which may be responsible for centering the tool, may remain generally in the same location with respect to the implant 108 while the blade 106 is rotated to plunge the distal point 150 in a distal direction to the underside of the implant 108. While the location of lateral point 154 is generally the same between the retracted position and the fully extended position of the blade 106, the orientation of the blade 106, and in turn the orientation of the lateral point 154, changes as exemplified in comparing FIG. 15 to FIG. 16.

The modified blade shape and offset configuration of the embodiments shown in FIGS. 15-20 further improve the ability of the blades 106 to traverse the entire tissue/bone contacting surface 109 of the implant 108 while maintaining adequate clearance around the implant rim. In contrast to the earlier embodiments shown in FIGS. 1-14, the blades 106 are positioned at a lateral and radial offset relative to the longitudinal axis of the tool 100. This offset allows the cutting paths of the blades 106 to follow a broader arc that more closely conforms to the curvature of the implant 108, ensuring that the blades can reach and cut along the full extent of the implant's outer surface. The offset positioning also enables the blades 106 to open to a wider degree without interference from the adjacent structure of the tool 100, thereby providing sufficient clearance to move past and over the lip of the implant 108 during positioning and removal. As a result, the tool 100 can be more easily seated around implants having thicker rims or deeper sockets while maintaining precise centering and continuous contact during the cutting motion. The combination of the modified blade geometry and the offset alignment thus enhances both the range of motion and functional accessibility of the blades 106 while maintaining the structural advantages of the preceding embodiments.

In some embodiments, as exemplified in FIGS. 15-20, the rotational axes of the arm segments and corresponding attachment structures 151 may be laterally and radially offset relative to the central longitudinal axis of the outer shaft 102. This offset configuration functions in a manner similar to that described in other embodiments, aiding in minimizing the overall lateral expanse of the cutting assembly 104 to reduce the incision size required for insertion of the tool 100 and to lessen the likelihood of unintentional contact with surrounding tissue. Additionally, offsetting the rotational axes increases the rigidity of the cutting assembly 104 and enhances the torque transmission from the internal shaft 122 through the arm segments to the blades 106. The result is a more efficient transfer of mechanical force, which improves the cutting performance and structural stability of the tool 100 during operation.

In some embodiments, as exemplified in FIGS. 15-20, the rotational axes of the arm segments and corresponding attachment structures 151 are laterally and radially offset relative to the central longitudinal axis of the outer shaft 102. This offset configuration functions in a manner similar to that described in other embodiments, aiding in minimizing the overall lateral expanse of the cutting assembly 104 to reduce the incision size required for insertion of the tool 100 and to lessen the likelihood of unintentional contact with surrounding tissue. In some aspects, the translation-support structure 134 may have an increased lateral dimension or modified geometry that further offsets the rotational axes of the arm segments relative to the longitudinal axis. This enlarged or reconfigured translation-support structure 134 enhances the mechanical leverage applied through the arm segments, thereby increasing the torque transmitted to the blades 106 and improving overall cutting efficiency. The combined offset of the translation-support structure 134 and the arm segments also increases the rigidity of the cutting assembly 104, resulting in a more stable and mechanically balanced tool 100 during use.

Some embodiments of the present invention include more than one outer shaft each with a cutting assembly configured to remove implants of particular sizes. Some embodiments include interchangeable blades configured to remove implants of particular sizes. Some embodiments include interchangeable cutting assemblies configured to remove implants of particular sizes.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. An implant removal tool, comprising:

an outer shaft and an internal shaft residing at least partially within the outer shaft;

the outer shaft in operable communication with a cutting assembly, the outer shaft defining a central longitudinal axis and including a distal end having an alignment structure configured to be received within an internal cavity of an implant;

the cutting assembly including a plurality of blades, each blade of the plurality of blades including an inwardly curving, wedge shape that tapers to a distal point;

at least one blade of the plurality of blades having a lateral side with a non-linear taper extending from a proximal, lateral point to the distal point;

wherein the plurality of blades are moveable between a retracted position and a fully extended position in which at least the distal points of the plurality of blades come together;

wherein manipulation of the internal shaft causes the plurality of blades to rotate between the retracted position and the fully extended position;

wherein the cutting assembly further includes a translation-support structure in operable engagement with the internal shaft such that movement of the internal shaft causes translation of the translation-support structure, and one or more support arms extending between the translation-support structure and the plurality of blades, each support arm of the one or more support arms including a first arm segment pivotably attached to the translation-support structure about a proximal rotational axis and a second arm segment operably attached to the first arm segment at a pivot joint, the second arm segment being pivotably attached to the outer shaft and non-rotatably secured to a corresponding blade of the plurality of blades, such that translation of the translation-support structure causes rotation of the corresponding blade, each proximal rotational axis being laterally offset relative to, and non-intersecting with, the central longitudinal axis;

wherein each blade of the plurality of blades is configured to move through a rotational plane containing an arcuate trajectory of the distal point as the blade rotates between the retracted position and the fully extended position, the rotational plane being laterally offset relative to the central longitudinal axis;

and wherein the non-linear taper of the at least one blade establishes multiple discontinuous contact regions circumferentially spaced about the central longitudinal axis when the plurality of blades are in the retracted position, the contact regions configured to center the tool relative to the implant.

2. The tool of claim 1, wherein each blade of the plurality of blades has a central longitudinal axis extending from a proximal end to the distal point and each blade of the plurality of blades is configured to move through the rotational plane that is offset and non-parallel to the central longitudinal axis of the respective blade.

3. The tool of claim 1, further including an attachment structure configured to operably couple each blade of the plurality of blades to the second arm segment of a corresponding one of the one or more support arms, wherein the attachment structure is secured to a proximal end of each blade of the plurality of blades at a location that is offset from a central longitudinal axis of the respective blade.

4. The tool of claim 1, further including:

each of the plurality of blades includes the lateral side with the non-linear taper and the multiple discontinuous contact regions include at least the proximal, lateral point and the distal point on the respective blade;

wherein the proximal, lateral point and the distal point on the respective blade are spaced apart along the non-linear taper to define an arcuate segment that is configured to remain in non-contacting relation with the implant when the plurality of blades are in or near the retracted position and centered about the implant.

5. The tool of claim 1, wherein the outer shaft includes one or more slots extending through the outer shaft proximate the distal end of the outer shaft, the internal shaft being configured to move relative to the outer shaft and including a distal stem, and the translation-support structure including inwardly extending retention members that extend through the one or more slots and abut the distal stem such that translation of the internal shaft causes translation of the translation-support structure.

6. The tool of claim 1, wherein each blade in the plurality of blades has a curvature that generally matches a curvature of the implant.

7. The tool of claim 1, wherein the plurality of blades consists of two blades, each of the two blades defining a cutting path configured to traverse between 25% and 50% of a tissue and/or bone contacting surface of the implant when the two blades are moved between the retracted and the fully extended positions.

8. The tool of claim 1, wherein the proximal, lateral point and the distal point of the at least one blade are sharpened to penetrate tissue and bone during centering of the tool.

9. An implant removal tool, comprising:

an outer shaft and an internal shaft residing at least partially within the outer shaft;

the outer shaft in operable communication with a cutting assembly, the outer shaft defining a central longitudinal axis and including a distal end having an alignment structure configured to be received within an internal cavity of an implant;

the cutting assembly including a plurality of blades, each blade of the plurality of blades including an inwardly curving, wedge shape that tapers from a proximal end to a distal point and a central longitudinal axis extending from the proximal end through the distal point;

wherein the plurality of blades are moveable between a retracted position and a fully extended position in which at least the distal points of the plurality of blades come together;

wherein manipulation of the internal shaft causes the plurality of blades to rotate between the retracted position and the fully extended position;

wherein the cutting assembly further includes a translation-support structure in operable engagement with the internal shaft such that movement of the internal shaft causes translation of the translation-support structure, and one or more support arms extending between the translation-support structure and the plurality of blades, each support arm of the one or more support arms including a first arm segment pivotably attached to the translation-support structure about a proximal rotational axis and a second arm segment operably attached to the first arm segment at a pivot joint, the second arm segment being pivotably attached to the outer shaft and non-rotatably secured to a corresponding blade of the plurality of blades, such that translation of the translation-support structure causes rotation of the corresponding blade, each proximal rotational axis being laterally offset relative to, and non-intersecting with, the central longitudinal axis of the outer shaft; and wherein each blade of the plurality of blades is configured to move through a rotational plane containing an arcuate trajectory of the distal point as the blade rotates between the retracted position and the fully extended position, that is offset and non-parallel with respect to the central longitudinal axis of the respective blade, the rotational plane being laterally offset relative to the central longitudinal axis of the respective blade.

10. The tool of claim 9, further including:

each blade of the plurality of blades having a lateral side with a non-linear taper extending from a proximal, lateral point to the distal point;

wherein the non-linear taper of each blade establishes multiple discontinuous contact regions spaced circumferentially about the central longitudinal axis of the outer shaft when the plurality of blades are in the retracted position; and wherein the contact regions are configured to collectively center the tool relative to the implant.

11. The tool of claim 10, wherein the multiple discontinuous contact regions include at least the proximal, lateral point and the distal point on each blade of the plurality of blades, with the proximal, lateral point and the distal point being spaced apart along the non-linear taper to define an arcuate segment of the respective blade that is configured to remain in non-contacting relation with the implant when the plurality of blades are in or near the retracted position and centered about the implant.

12. The tool of claim 10, wherein the proximal, lateral point and the distal point of each blade of the plurality of blades are sharpened to penetrate tissue and bone during centering of the tool.

13. The tool of claim 9, wherein the outer shaft includes one or more slots extending through the outer shaft proximate the distal end of the outer shaft, the internal shaft being configured to move relative to the outer shaft and including a distal stem, and the translation-support structure including inwardly extending retention members that extend through the one or more slots and abut the distal stem such that translation of the internal shaft causes translation of the translation-support structure.

14. The tool of claim 9, further including an attachment structure configured to operably couple each blade of the plurality of blades to the second arm segment of a corresponding one of the one or more support arms, wherein the attachment structure is secured to the proximal end of each blade of the plurality of blades at a location that is offset from the central longitudinal axis of the respective blade.

15. The tool of claim 9, wherein each blade in the plurality of blades has a curvature that generally matches a curvature of the implant.

16. The tool of claim 9, wherein the plurality of blades consists of two blades, each of the two blades configured to define a cutting path configured to traverse between 25% and 50% of a tissue and/or bone contacting surface of the implant when the two blades are moved between the retracted and the fully extended positions.

17. An implant removal tool, comprising:

an outer shaft and an internal shaft residing at least partially within the outer shaft;

the outer shaft in operable communication with a cutting assembly, the outer shaft defining a central longitudinal axis and including a distal end having an alignment structure configured to be received within an internal cavity of an implant;

the cutting assembly including a pair of blades, the pair of blades being the only blades of the cutting assembly, each blade of the pair of blades being movable between a retracted position and a fully extended position;

wherein each blade of the pair of blades includes an inwardly curving, wedge shape having a taper that extends toward a distal point of the respective blade;

wherein the cutting assembly further includes a translation-support structure in operable engagement with the internal shaft such that movement of the internal shaft causes translation of the translation-support structure, and one or more support arms extending between the translation-support structure and the pair of blades, each support arm of the one or more support arms including a first arm segment pivotably attached to the translation-support structure about a proximal rotational axis and a second arm segment operably attached to the first arm segment at a pivot joint, the second arm segment being pivotably attached to the outer shaft and non-rotatably secured to a corresponding blade of the pair of blades, such that translation of the translation-support structure causes movement of the corresponding blade between the retracted position and the fully extended position, each proximal rotational axis being laterally offset relative to, and non-intersecting with, the central longitudinal axis;

wherein each blade of the pair of blades is configured to move through a rotational plane containing an arcuate trajectory of the distal point as the blade moves between the retracted position and the fully extended position, the rotational plane being laterally offset relative to the central longitudinal axis;

wherein, when the pair of blades are in or near the retracted position, each blade of the pair of blades defines multiple discontinuous and spaced contact regions arranged circumferentially about the central longitudinal axis, the contact regions of the pair of blades being collectively configured to center the tool relative to the implant; and wherein manipulation of the internal shaft causes the pair of blades to move between the retracted position and the fully extended position.

18. The tool of claim 17, wherein each blade of the pair of blades has a central longitudinal axis extending from a proximal end toward the distal point, and each blade of the pair of blades is configured to move through the rotational plane that is offset and non-parallel relative to the central longitudinal axis of the respective blade.

19. The tool of claim 17, wherein each of the pair of blades includes a lateral side having a non-linear taper, and the multiple, spaced contact regions on each blade of the pair of blades are defined along the non-linear taper such that a portion of each blade of the pair of blades between the contact regions is configured to remain in non-contacting relation when the tool is centered on the implant and the pair of blades are in or near the retracted position.

20. The tool of claim 17, wherein the pair of blades are configured to define a cutting path configured to traverse between 25% and 50% of a tissue-contacting surface of the implant when the pair of blades are moved between the retracted and the fully extended positions.

* * * * *